United States Patent
Chang

(10) Patent No.: US 9,375,590 B2
(45) Date of Patent: Jun. 28, 2016

(54) RESPIRATOR MASK DEVICE

(71) Applicant: Hsiner Co., LTD., Taichung (TW)

(72) Inventor: Eric Chang, Taichung (TW)

(73) Assignee: Hsiner Co., Ltd., Taichung (TW)

( * ) Notice: Subject to any disclaimer, the term of this patent is extended or adjusted under 35 U.S.C. 154(b) by 263 days.

(21) Appl. No.: 14/077,324

(22) Filed: Nov. 12, 2013

(65) Prior Publication Data

US 2014/0345620 A1   Nov. 27, 2014

(30) Foreign Application Priority Data

May 27, 2013   (TW) .............................. 102118626 A

(51) Int. Cl.
*A61M 16/06* (2006.01)
*A62B 18/08* (2006.01)

(52) U.S. Cl.
CPC .................................... *A62B 18/084* (2013.01)

(58) Field of Classification Search
CPC . A61M 16/00; A61M 16/06; A61M 16/0605; A61M 16/0616; A61M 16/0622; A61M 16/0627; A61M 16/0633; A61M 16/0638; A61M 16/0644; A61M 16/0645
See application file for complete search history.

(56) References Cited

U.S. PATENT DOCUMENTS

| | | | |
|---|---|---|---|
| 6,374,826 | B1 | 4/2002 | Gunaratnam et al. |
| 7,600,513 | B2 | 10/2009 | Gunaratnam et al. |
| 8,210,181 | B2 | 7/2012 | Gunaratnam et al. |
| 8,365,735 | B2 | 2/2013 | Chang |
| 2007/0044804 | A1 | 3/2007 | Matula, Jr. et al. |
| 2015/0083124 | A1* | 3/2015 | Chodkowski ..... A61M 16/0683 128/202.27 |

FOREIGN PATENT DOCUMENTS

WO   WO 9720597 A1 *   6/1997 ............ A61M 16/06

* cited by examiner

*Primary Examiner* — Melanie Hand
(74) *Attorney, Agent, or Firm* — Curatolo Sidoti Co., LPA; Joseph G. Curatolo; Salvatore A. Sidoti

(57) ABSTRACT

A respirator mask device includes a frame unit, a mask shell connected pivotally to the frame unit, a mask cushion secured to the mask shell, an adjusting unit operable for adjusting relative position between an upper end of the mask shell and the frame unit, two connecting pieces disposed respectively on left and right sides of a lower end of the frame unit and connected pivotally to the mask shell, two first engaging members disposed respectively on the left and right sides of the lower end of the extension frame, and a head strip unit. The head strap unit includes a strap body, and two second engaging members disposed on the strap body and connected respectively and removably to the first engaging members.

5 Claims, 12 Drawing Sheets

RESPIRATOR MASK DEVICE

CROSS-REFERENCE TO RELATED APPLICATION

This application claims priority of Taiwanese Application No. 102118626, filed on May 27, 2013.

BACKGROUND OF THE INVENTION

1. Field of the Invention

This invention relates to a medical device, and more particularly to a respirator mask device.

2. Description of the Related Art

Referring to FIG. 1, a conventional respirator mask device disclosed in U.S. Pat. No. 6,374,826 includes a head strap 100, a forehead frame 120, and a mask body 130. The head strap 100 has a head engaging portion 101 for contact with the head of a patient, and four connecting portions 110 for connection with the forehead frame 120 and the mask body 130. The forehead frame 120 and the mask body 130 are provided with loops 140 permitting the head strap 100 to pass therethrough. The connecting portions 110 of the head strap 100 have distal ends that are attached to the head engaging portion 101 by means of hook-and-loop fasteners 150, such that the conventional respirator mask device can be sleeved on the head of the patient under appropriate pressure, thereby providing a comfort feeling to the patient. However, it is necessary to adjust frequently the positions of the hook-and-loop fasteners 150, thereby resulting in inconvenience during use.

To solve this problem, referring to FIG. 2, U.S. Pat. Nos. 7,600,513 and 8,210,181 disclose another respirator mask device that includes a rigid frame 210 and an adjustable strap 220. The frame 210 has a female connector 230. The strap 220 has a male connector 240 snap fitted into the female connector 230. However, such an arrangement is not suitable for different patients. The devices disclosed in U.S. Patent Application Publication NO. 20070044804 and U.S. Pat. No. 8,365,735 can solve this problem. However, in these devices, the position of a mask body needs to be adjusted relative to the frame.

For example, referring to FIGS. 3 and 4, a respirator mask device disclosed in U.S. Pat. No. 8,365,735 includes a mask unit 310, a frame unit 320, and a head strip 330. The mask unit 310 is connected pivotally to the frame unit 320 by a pivotal connection unit 340, and is pivotable relative to the frame unit 320 to make the device closer to the face of a patient. Due to the presence of the pivotal connection unit 340, the volume of an assembly of the frame unit 320 and the mask unit 310 is increased significantly, which does not meet the requirement of miniaturization. Furthermore, it is time-consuming to interconnect the frame unit 320 and the head strap 330, thereby resulting in inconvenience when used in a hospital.

SUMMARY OF THE INVENTION

The object of this invention is to provide a respirator mask device that can overcome the above-mentioned disadvantages associated with the prior art.

According to this invention, a respirator mask device includes a frame unit, a mask shell connected pivotally to the frame unit, a mask cushion secured to the mask shell, an adjusting unit operable for adjusting relative position between an upper end of the mask shell and the frame unit, two connecting pieces disposed respectively on left and right sides of a lower end of the frame unit and connected pivotally to the mask shell, two first engaging members disposed respectively on the left and right sides of the lower end of the extension frame, and a head strip unit. The head strap unit includes a strap body, and two second engaging members disposed on the strap body and connected respectively and removably to the first engaging members.

Through pivotal connection between the frame unit and the mask shell, the mask unit can be attached to the face of a patient under appropriate pressure. Furthermore, since the frame unit is connected to the mask shell and the head strap unit at the left and right sides thereof, the volume of an assembly of the frame unit and the mask unit is reduced to meet the miniaturization requirement.

BRIEF DESCRIPTION OF THE DRAWINGS

These and other features and advantages of this invention will become apparent in the following detailed description of a preferred embodiment of this invention, with reference to the accompanying drawings, in which.

DETAILED DESCRIPTION OF THE PREFERRED EMBODIMENT

Figure 1:
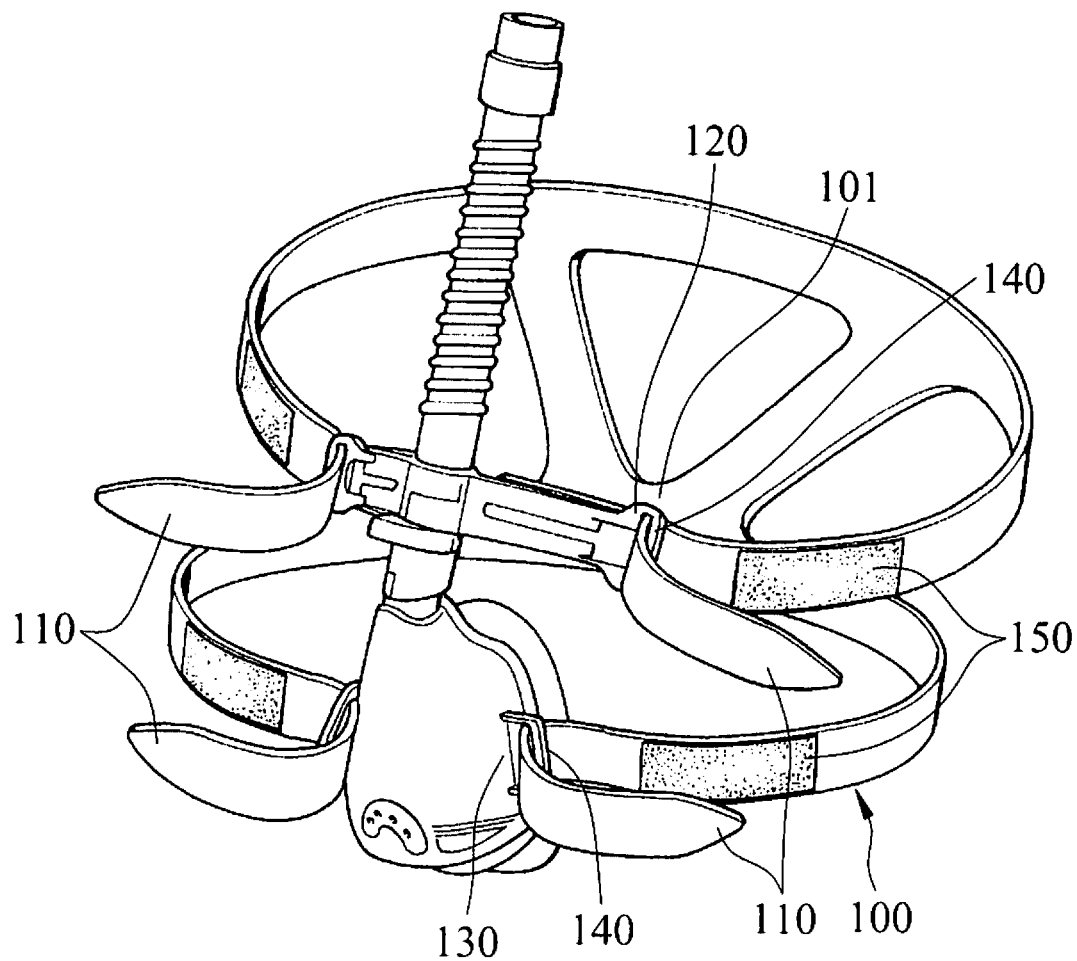
FIGS. 1 to 3 are perspective views showing respectively three conventional respirator mask devices.
Figure 2:
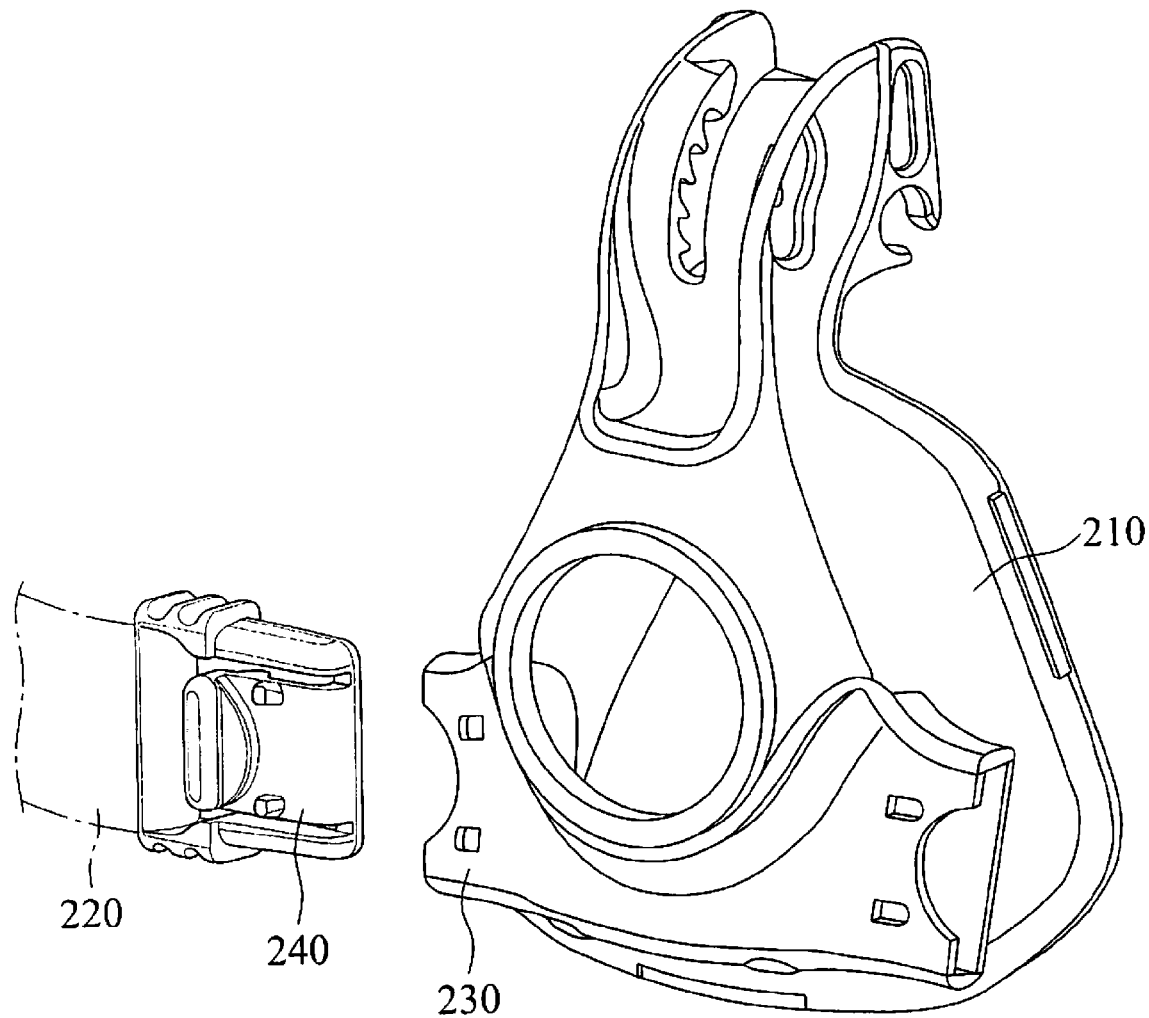
Figure 3:
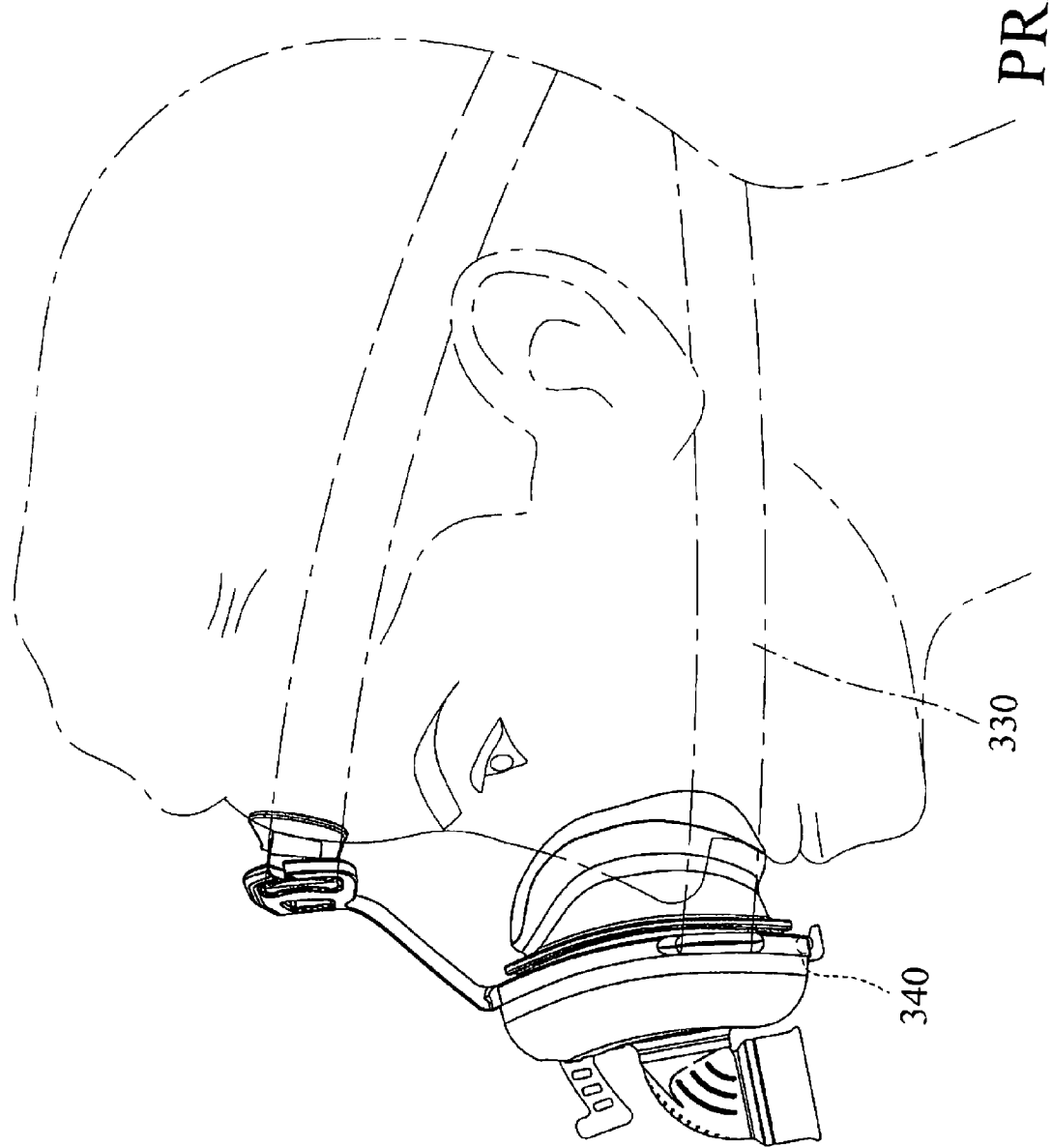
Figure 4:
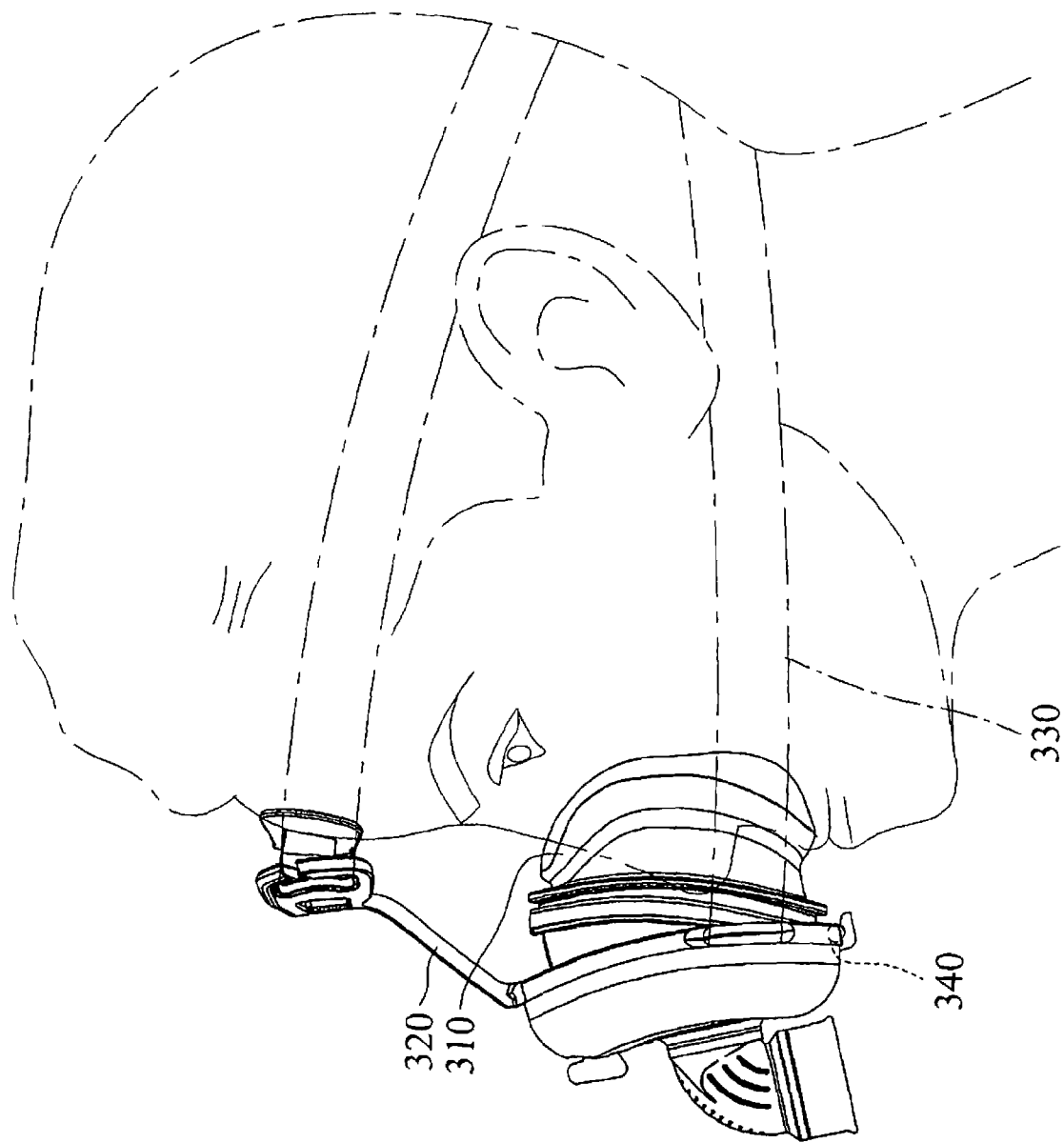
FIG. 4 is a view similar to FIG. 3, illustrating how to adjust the corresponding conventional respirator mask device.
Figure 5:
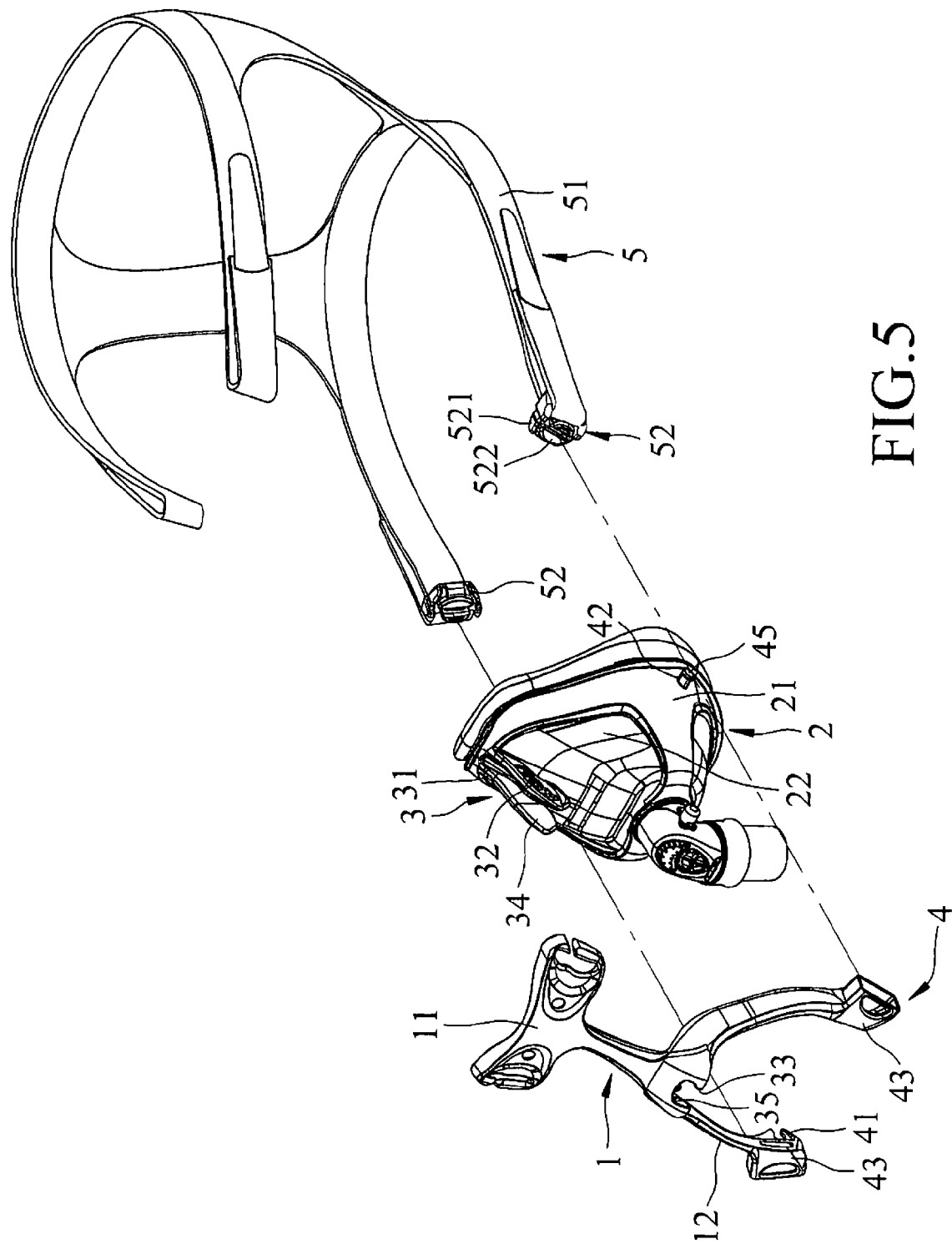
FIG. 5 an exploded perspective view of the preferred embodiment of a respirator mask device according to this invention.
Figure 6:
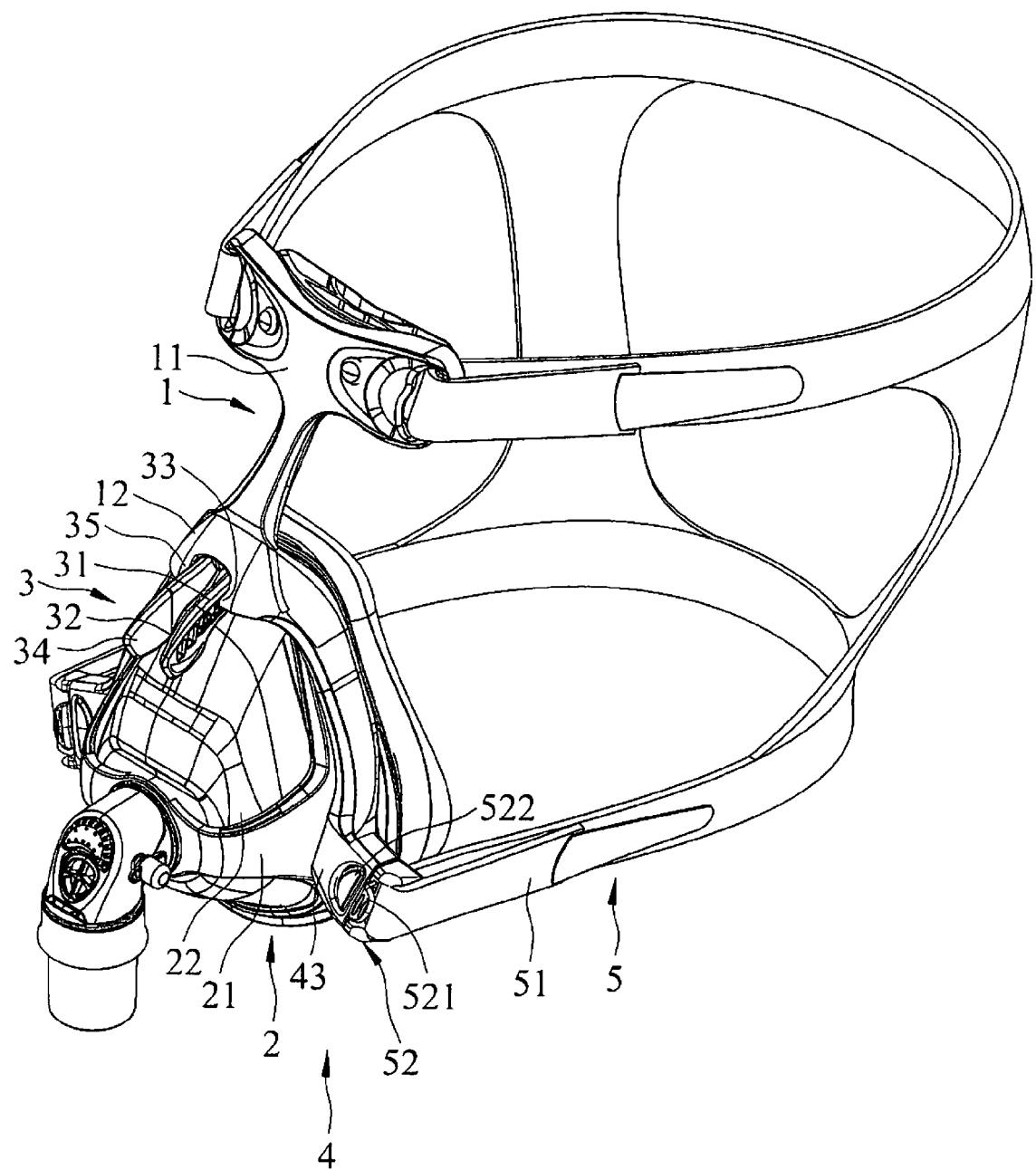
FIG. 6 is an assembled perspective view of the preferred embodiment.
Figure 7:
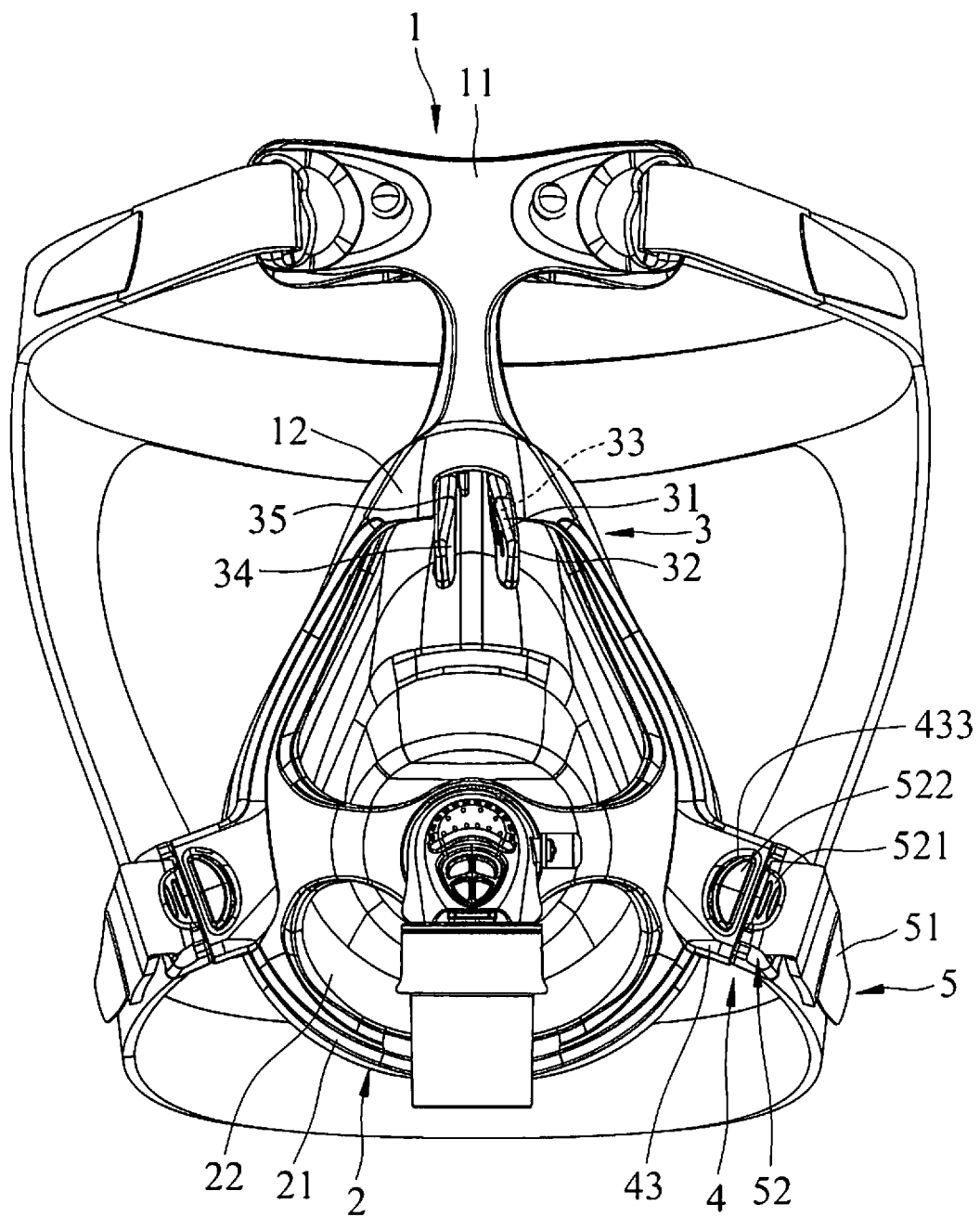
FIG. 7 is a front view of the preferred embodiment.
Figure 8:
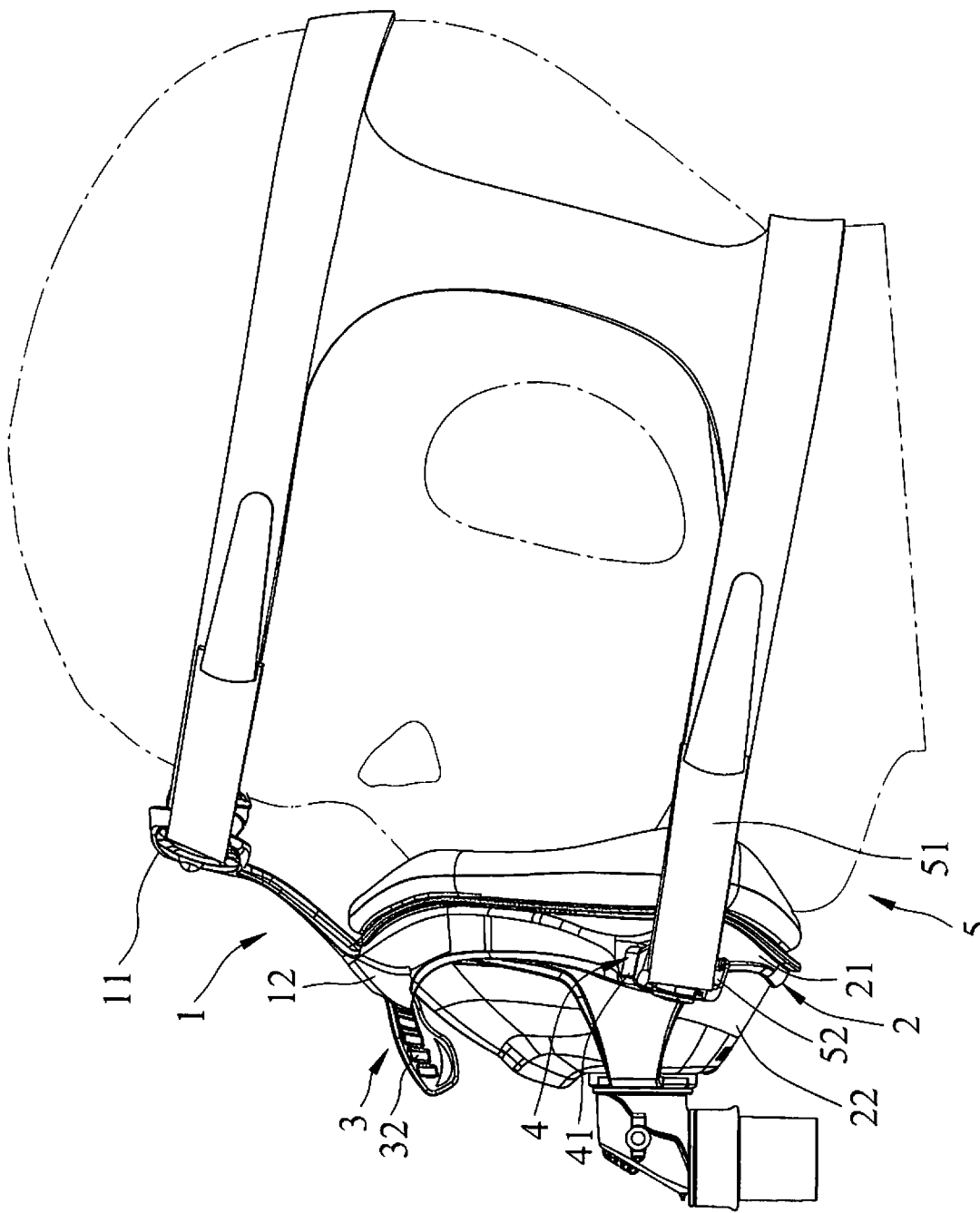
FIG. 8 is a side view illustrating a position of the mask unit relative to the frame unit.
Figure 9:
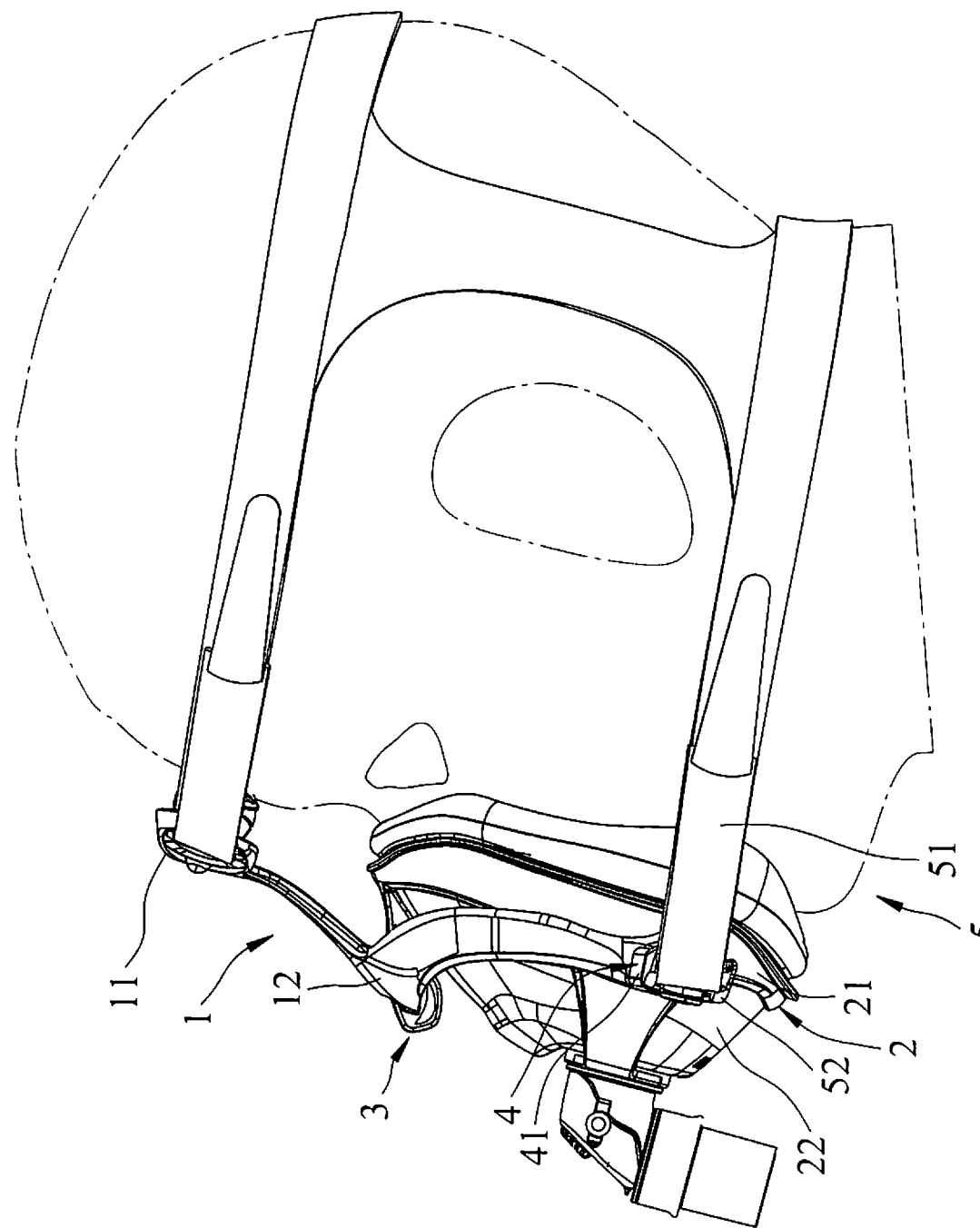
FIG. 9 is a view similar to FIG. 8 but illustrating another position of the mask unit relative to the frame unit.

Referring to FIGS. 5, 6, and 7, the preferred embodiment of a respirator mask device according to this invention includes a frame unit 1, a mask unit 2, an adjusting unit 3, a connecting unit 4, and a head strap unit 5.

The frame unit 1 includes a forehead frame 11, and an extension frame 12 extending downwardly from the forehead frame 11.

The mask unit 2 includes a mask shell 21 connected pivotally to the extension frame 12, and a mask cushion 22 secured to the mask shell 21.

Figure 5A:
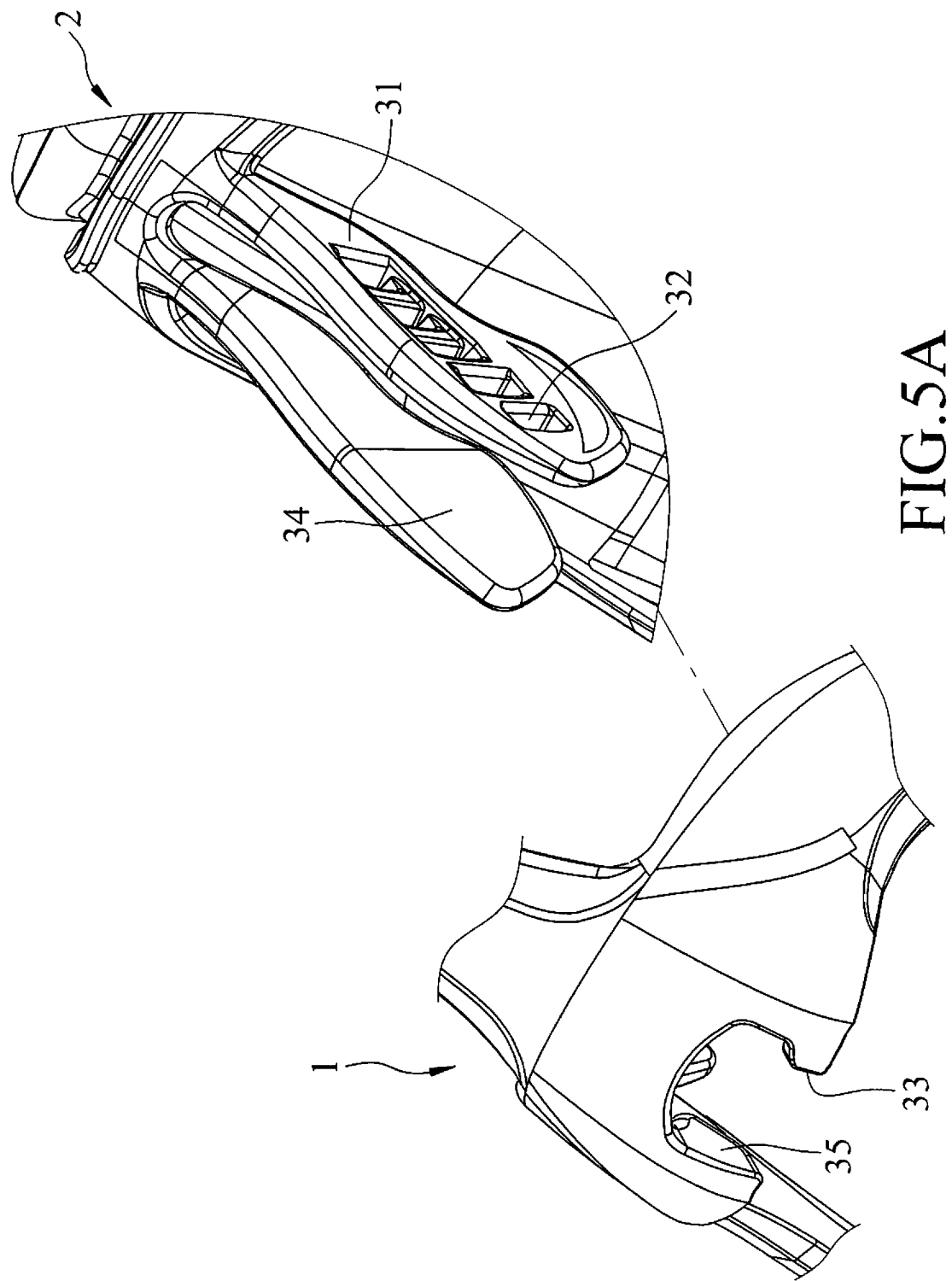
FIG. 5A is a fragmentary exploded perspective view of a mask unit and a frame unit of the preferred embodiment.
Figure 5B:
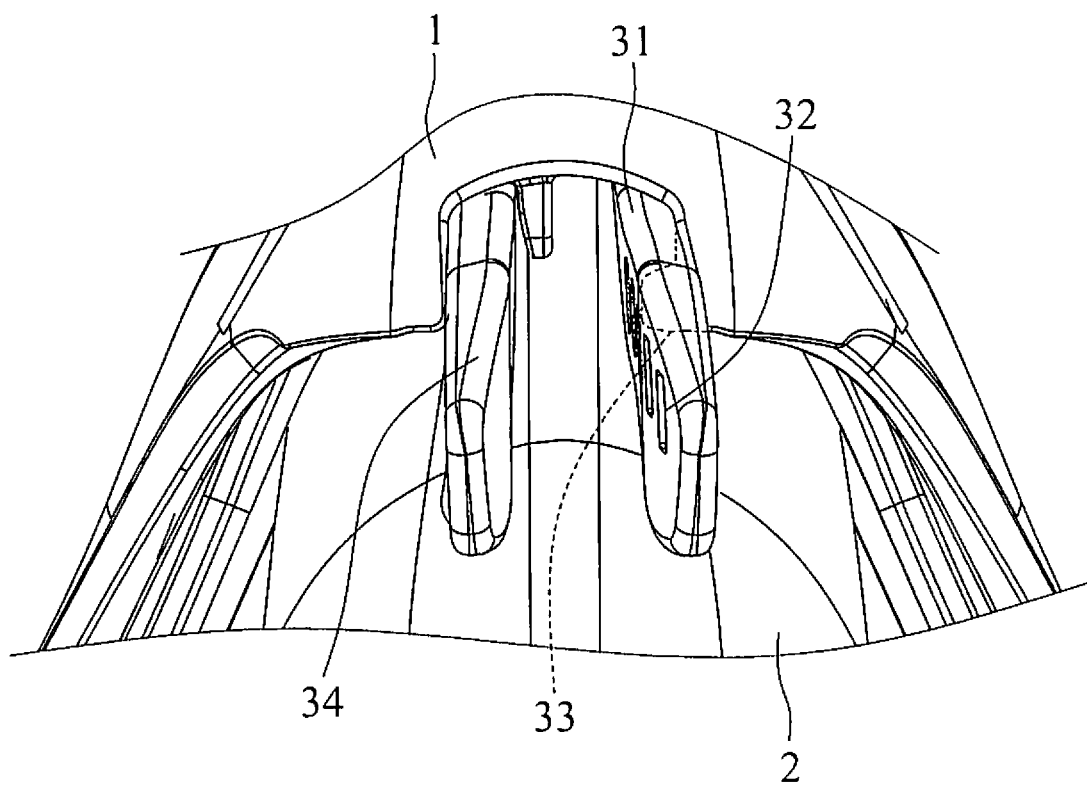
FIG. 5B is a fragmentary perspective view of an adjustment plate and a sliding rail of the mask unit of the preferred embodiment.

With further reference to FIGS. 5A and 5B, the adjusting unit 3 is operable for adjusting relative position between an upper end of the mask shell 21 and the extension frame 22. The adjusting unit 3 includes an adjustment plate 31 disposed on the upper end of the mask shell 21, a plurality of positioning holes 32 formed in the adjustment plate 31, and an insert member 33 disposed on the extension frame 12 and inserted removably into a selected one of the positioning holes 32, so as to position the upper end of the mask shell 21 relative to the extension frame 12.

The adjustment plate 31 is formed integrally with the upper end of the mask shell 21. The insert member 33 is formed integrally with the extension frame 12. The adjusting unit 3 further includes a sliding rail 34 extending from the upper end of the mask shell 21, and a sliding block 35 extending from the extension fame 12. The sliding rail 34 is generally parallel to the adjusting plate 31, and has upper and lower ends aligned respectively with those of the adjustment plate 31. The sliding block 35 is aligned with the insert member 33.

During operation of the adjusting unit 3, it is only necessary to engage the insert member 33 with the desired positioning hole 32. As such, the adjusting unit 3 is convenient to operate.

The connecting unit 4 includes two connecting pieces 41, two pivot pins 42, and two first engaging members 43. The connecting pieces 41 are formed respectively with left and right sides of a lower end of the extension frame 12, and is connected pivotally to the mask unit 2. The pivot pins 42 are formed respectively with left and right sides of a lower end of the mask shell 21. The first engaging members 43 are formed respectively with the left and right sides of a lower end of the extension frame 12. Each of the pivot pins 42 has an end flange 45 extending radially and outwardly from an end thereof. The connecting pieces 41 are connected respectively and pivotally to the pivot pins 42. In this embodiment, each of the connecting pieces 41 is configured as a C-shaped retaining ring, and is sleeved tightly on the corresponding pivot pin 42 between the mask shell 21 and the end flange 45 of the corresponding pivot pin 42. As such, removal of the connecting pieces 41 from the pivot pins 42 is prevented.

Figure 5C:
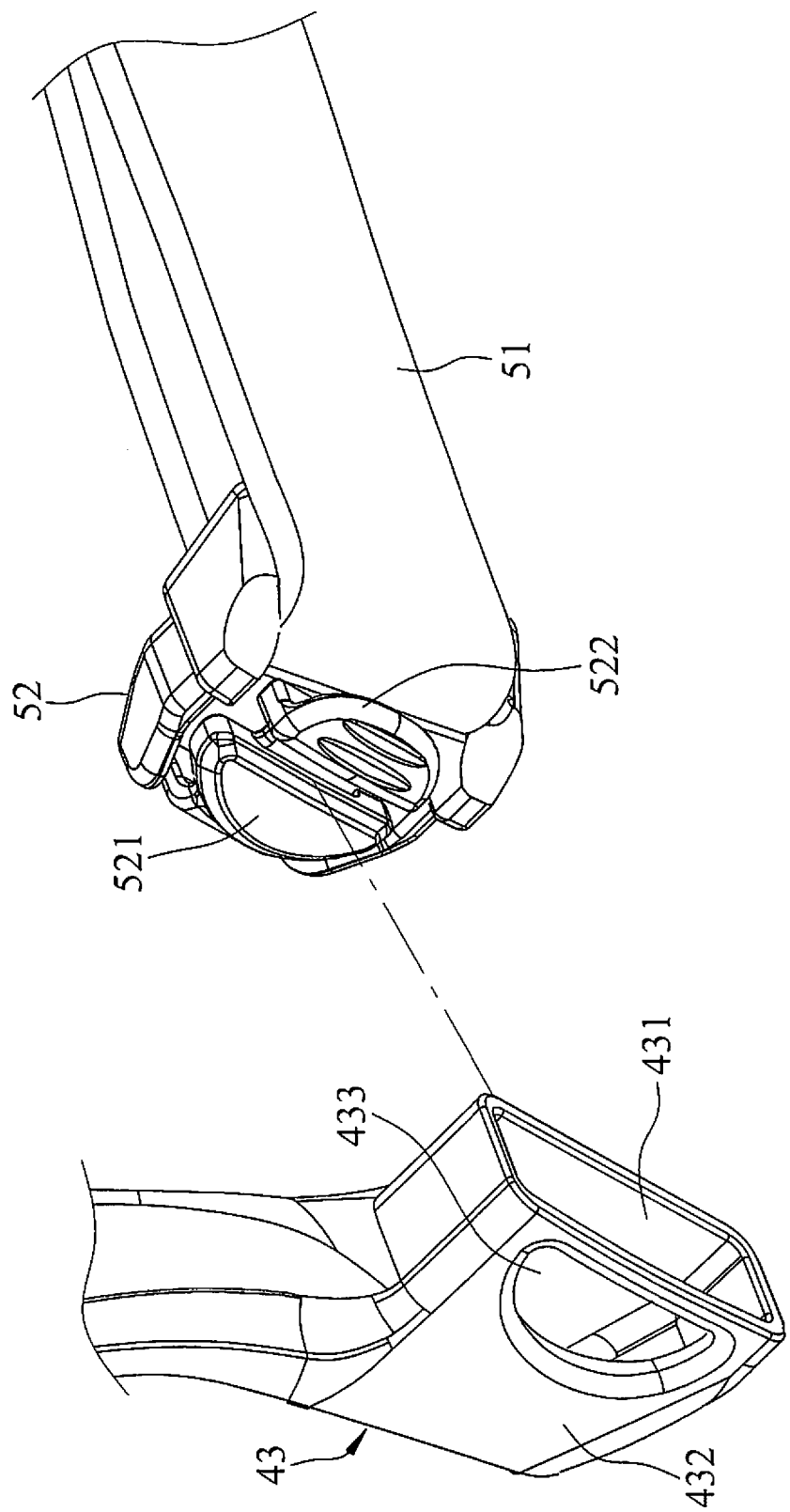
FIG. 5C is a fragmentary exploded perspective view of the frame unit and a head strap unit of the preferred embodiment.

With further reference to FIG. 5C, the head strap unit 5 includes a strap body 51, and two second engaging members 52 disposed on the strap body 51. The second engaging members 52 are connected respectively and removably to the first engaging members 43. Each of the first engaging members 43 is tubular, and has an end opening 431, a surrounding wall 432 defining the end opening 431, and a retaining hole 433 formed in the surrounding wall 432. The second engaging members 52 are inserted respectively into the end openings 931 in the first engaging members 43. Each of the second engaging members 52 includes a resilient engaging portion 521 engaging removably the retaining hole 433 in the corresponding first engaging member 43, and a pressing plate 522 extending from the resilient engaging portion 521 and exposed outwardly from the end opening 431 in the corresponding first engaging member 43 such that, the pressing plate 522 can be pressed to remove the resilient engaging portion 521 from the retaining hole 433 in the corresponding first engaging member 43, thereby allowing for removal of the corresponding second engaging member 52 from the corresponding first engaging member 43.

In view of the above, the mask unit 2 is connected pivotally to the frame unit 1 by the connecting unit 4, so that the position of the mask unit 2 relative to the frame unit 1 can be adjusted easily. Furthermore, since the connecting unit 4 is disposed at left and right sides of the frame unit 1 and the mask unit 2, the volume of an assembly of the frame unit 1 and the mask unit 2 can be reduced. Thus, the object of this invention is achieved.

With this invention thus explained, it is apparent that numerous modifications and variations can be made without departing from the scope and spirit of this invention. It is therefore intended that this invention be limited only as indicated by the appended claims.

I claim:

1. A respirator mask device comprising:
   a frame unit including a forehead frame, and an extension frame extending downwardly from said forehead frame;
   a mask unit including a mask shell connected pivotally to said extension frame, and a mask cushion secured to said mask shell;
   an adjusting unit operable for adjusting relative position between an upper end of said mask shell and said extension frame, said adjusting unit including an adjustment plate disposed on said upper end of said mask shell, a plurality of positioning holes formed in said adjustment plate, and an insert member disposed on said extension frame and inserted removably into a selected one of said positioning holes so as to position said upper end of said mask shell relative to said extension frame;
   a connecting unit including two connecting pieces disposed respectively on left and right sides of a lower end of said extension frame and connected pivotally to said mask unit, and two first engaging members disposed respectively on said left and right sides of said lower end of said extension frame; and
   a head strap unit including a strap body, and two second engaging members disposed on said strap body and connected respectively and removably to said first engaging members;
   wherein said connecting pieces of said connecting unit are formed integrally with said frame unit, and said adjusting unit further includes two pivot pins formed integrally with said mask shell and connected respectively and pivotally to said connecting pieces.

2. The respirator mask device as claimed in claim 1, wherein:
   each of said first engaging members is tubular, and has an end opening, a surrounding wall defining said end opening, and a retaining hole formed in said surrounding wall; and
   said second engaging members are inserted respectively into said end openings in said first engaging members, each of said second engaging members including a resilient engaging portion engaging removably said retaining hole in a responding one of said first engaging members, and a pressing plate extending from said engaging portion and exposed outwardly from said end opening of said corresponding one of said first engaging members such that, said pressing plate can be pressed to remove said resilient engaging portion from said retaining hole in said corresponding one of said first engaging members, thereby allowing for removal of a corresponding one of said second engaging members from said corresponding one of said first engaging members.

3. The respirator mask device as claimed in claim 1, wherein each of said pivot pins of said connecting unit has an end flange extending radially and outwardly from an end thereof, each of said connecting pieces being sleeved on a corresponding one of said pivot pins between said mask shell and said end flange of said corresponding one of said pivot pins.

4. The respirator mask device as claimed in claim 1, wherein each of said connecting pieces is configured as a C-shaped retaining ring that is sleeved tightly on a corresponding one of said pivot pins.

5. The respirator mask device as claimed in claim 1, wherein said adjustment plate is formed integrally with said upper end of said mask shell, said insert member being formed integrally with said extension frame, said adjusting unit further including a sliding rail extending integrally from said upper end of said mask shell, and a sliding block extending integrally from said extension frame, said sliding rail being generally parallel to said adjustment plate, and having upper and lower ends aligned respectively with those of said adjustment plate, said sliding block being aligned with said insert member.

* * * * *